(12) United States Patent  (10) Patent No.: US 6,595,963 B1
Barbut  (45) Date of Patent: Jul. 22, 2003

(54) AORTIC SHUNT FOR SELECTIVE CEREBRAL PERFUSION IN STROKE AND CARDIAC ARREST

(75) Inventor: Denise R. Barbut, New York, NY (US)

(73) Assignee: CoAxia, Inc., Maple Grove, MN (US)

(*) Notice: Subject to any disclaimer, the term of this patent is extended or adjusted under 35 U.S.C. 154(b) by 121 days.

(21) Appl. No.: 09/658,482

(22) Filed: Sep. 7, 2000

(51) Int. Cl.[7] ............................................... A61M 5/00
(52) U.S. Cl. ............................ 604/246; 604/9; 604/34; 604/6.13
(58) Field of Search .................. 604/8, 9, 34, 6.13, 604/113, 291, 246, 247; 606/159

(56) References Cited

U.S. PATENT DOCUMENTS

| | | | | |
|---|---|---|---|---|
| 5,195,976 A | * | 3/1993 | Swenson | 604/113 |
| 5,308,320 A | * | 5/1994 | Safar et al. | 604/113 X |
| 5,738,649 A | | 4/1998 | Macoviak | 604/43 |
| 5,827,237 A | | 10/1998 | Macoviak et al. | 604/246 |
| 5,833,671 A | | 11/1998 | Macoviak et al. | 604/247 |
| 5,928,181 A | * | 7/1999 | Coleman et al. | 604/8 |
| 6,010,522 A | * | 1/2000 | Barbut et al. | 606/159 X |
| 6,139,517 A | * | 10/2000 | Macoviak et al. | 604/8 |

* cited by examiner

Primary Examiner—Harry B. Tanner
(74) Attorney, Agent, or Firm—O'Melveny & Myers LLP

(57) ABSTRACT

An aortic shunt comprising a second tubular member nested within a lumen of a first tubular member, wherein aortic blood flows through the lumen of the first tubular member and oxygenated and/or cooled blood is infused through a lumen and distal port(s) of the second tubular member to perfuse the cerebral vasculature. Alternatively, a cooling cylinder is nested within the first member, such that aortic blood is cooled through the cylinder before being delivered to the brain. A venous return catheter comprising an elongate tubular member is also provided to remove and isolate the cooled blood entering through jugular veins from the blood entering through the subclavian veins, when the cannula is positioned in the superior vena cava. Methods of using the aortic shunt and/or venous return cannula in providing selective cerebral perfusion in patients suffering from stroke and cardiac arrest are also disclosed.

33 Claims, 7 Drawing Sheets

AORTIC SHUNT FOR SELECTIVE CEREBRAL PERFUSION IN STROKE AND CARDIAC ARREST

FIELD OF THE INVENTION

The present invention relates generally to medical devices. More particularly, the invention relates to methods and devices for selectively diverting blood flow to the cerebral vasculature from the aorta in patients having stroke or cardiac arrest. More particularly, the invention relates to apparatus and methods which provide an aortic shunt and a venous return cannula for augmenting and/or cooling oxygenated blood to the brain. The devices and methods also provide mechanisms for variable blood flow through the aorta.

BACKGROUND OF THE INVENTION

Patients experiencing cerebral ischemia often suffer from disabilities ranging from transient neurological deficit to irreversible damage (stroke) or death. Cerebral ischemia, i.e., reduction or cessation of blood flow to the central nervous system, can be characterized as either global or focal. Global cerebral ischemia refers to reduction of blood flow within the cerebral vasculature resulting from systemic circulatory failure caused by, e.g., shock, cardiac failure, or cardiac arrest. Within minutes of circulatory failure, tissues become ischemic, particularly in the heart and brain.

Cardiac arrest is defined as abrupt cessation of cardiac pump function, e.g., from myocardial infarction with loss of substantial muscle mass, acute myocarditis, or from depression of myocardial contractility following prolonged cardiopulmonary bypass. Mechanical abnormalities, such as severe valvular stenosis, massive aortic or mitral regurgitation, acutely acquired ventricular septal defects, can also cause cardiac arrest by reducing cardiac output. Additional causes of cardiac arrest include arrhythmia, such as ventricular fibrillation and ventricular tachycardia.

With sudden cessation of blood flow to the brain, complete loss of consciousness is a sine qua non in cardiac arrest. Cardiac arrest often progresses to death within minutes if active interventions, e.g., cardiopulmonary resuscitation (CPR), defibrillation, use of inotropic agents and vasoconstrictors such as dopamine, dobutamine, or epinephrine, are not undertaken promptly. The most common cause of death during hospitalization after resuscitated cardiac arrests are related to the severity of ischemic injury to the central nervous system, e.g., anoxic encephalopathy. The ability to resuscitate patients of cardiac arrest is related to the time from onset to institution of resuscitative efforts, the mechanism, and the clinical status of the patient prior to the arrest.

Focal cerebral ischemia refers to cessation or reduction of blood flow within the cerebral vasculature resulting from a partial or complete occlusion in the intracranial or extracranial cerebral arteries. Such occlusion typically results in stroke, a syndrome characterized by the acute onset of a neurological deficit that persists for at least 24 hours, reflecting focal involvement of the central nervous system and is the result of a disturbance of the cerebral circulation. Other causes of focal cerebral ischemia include vasospasm due to subarachnoid hemorrhage or iatrogenic intervention.

Traditionally, emergent management of acute ischemic stroke consists of mainly general supportive care, e.g. hydration, monitoring neurological status, blood pressure control, and/or anti-platelet or anti-coagulation therapy. Since 1996, tissue plasminogen activator (t-PA) or Activase®, was approved by the FDA for treatment of acute stroke. However, treatment with systemic t-PA is associated with increased risk of intracerebral hemorrhage and other hemorrhagic complications. Aside from the administration of thrombolytic agents and heparin, there are no therapeutic options currently on the market for patients suffering from occlusion focal cerebral ischemia. Vasospasm may be partially responsive to vasodilating agents. The newly developing field of neurovascular surgery, which involves placing minimally invasive devices within the carotid arteries to physically remove the offending lesion may provide a therapeutic option for these patients in the future, although this kind of manipulation may lead to vasospasm itself.

In both stroke and cardiac arrest, patients develop neurological deficits due to reduction in cerebral blood flow. Treatments should include measures to increase blood flow to the cerebral vasculature to maintain viability of neural tissue, thereby increasing the length of time available for interventional treatment and minimizing neurologic deficit while waiting for resolution of the ischemia.

New devices and methods are thus needed for augmentation of cerebral blood flow in treating patients with either stroke or cardiac arrest caused by reduced cerebral perfusion, thereby minimizing neurologic deficits.

SUMMARY OF THE INVENTION

The invention provides vascular constriction devices and methods for augmenting blood flow to a patient's cerebral vasculature, including the carotid and vertebral arteries, while maintaining peripheral circulation. The devices constructed according to the present invention comprise an aortic shunt, having first and second tubular members. The first member has a first diameter suitable for passage through the aortic lumen and is expandable to a second diameter suitable for frictionally engaging the aortic lumen. In certain embodiments, the first member comprises a self-expanding stent, or an expandable cylindrical or toroidal balloon. The first member has a length which spans from the ascending aorta upstream of the brachiocephalic trunk to the descending aorta downstream of the left subclavian artery. The first member also includes a lumen that communicates with proximal and distal openings, and a side opening adapted to communicate with the carotid arteries.

The second tubular member is nested within the first tubular member. The second member includes a lumen communicating with proximal and distal openings. The distal opening is aligned with the side opening of the first tubular member. This structure allows blood flow through the ascending aorta through the first member into the descending aorta, and through the second tubular member into the carotid arteries.

In another embodiment, the distal end of the second tubular member communicates with a port or a plurality of ports mounted on an intermediate portion of the first tubular member. The port(s) are adapted to communicate with the carotid arteries. The proximal end of the second tubular member extends through an incision on a peripheral artery, e.g., femoral artery, outside of a patient's body and is adapted to receive infusion of oxygenated blood or cooled solution, which passes through the lumen and port(s) of the second tubular member into the carotid arteries.

In another embodiment, a cooling coil is included in the second member for cooling blood passing through the second member before flowing into the carotid arteries. A thermometer is optionally mounted in the first member, second member, and/or the cooling coil for measuring temperature of blood flow upstream and downstream the device and into the carotid arteries. In certain embodiments, a pump and a mechanism are included in the second member to, respectively, facilitate and to provide variable blood flow from the aorta into the carotid arteries.

The present invention also provides venous return cannulas for receiving blood from the cerebral venous circulation. When used in conjunction with the aortic shunts described above, the venous return cannulas allow the cerebral circulation to be isolated from the systemic circulation in selective cooling of the cerebral circulation. This is particularly helpful in minimizing complications associated with systemic cooling, e.g., disseminated intravascular coagulation (DIC). The cannula has an elongate tubular member having a lumen communicating with a proximal end and a port at a distal end. The distal port is adapted to receive venous blood from the jugular veins. An inflatable chamber is included in the distal end, and when expanded, is adapted to engage the lumens of the right and left subclavian veins at a position where the jugular veins and the subclavian veins join the superior vena cava. The chamber also includes first and second ports that are adapted to receive blood from the right and left subclavian veins and pass the blood into the superior vena cava.

In using the aortic shunts described above for treating patient with stroke and/or cardiac arrest, the aortic shunt is first advanced into the aorta through an incision on a peripheral artery, e.g., the femoral artery. The shunt is positioned so that the proximal opening of the first tubular member is upstream of the brachiocephalic trunk, the distal opening of the first tubular member is downstream of the left subclavian artery, and the side opening communicates with the carotid arteries. The shunt is expanded so that the first tubular member engages the lumen of the aorta. Oxygenated blood flows from the ascending aorta through the first tubular member into the descending aorta and through the second tubular member into the carotid arteries. Blood is cooled when passed through the second member. Alternatively, cooled oxygenated blood or neuroprotective solution is infused through the proximal end of the second tubular member and passed through the ports mounted on an intermediate portion of the first tubular member. Blood flow to the brain can be varied by varying the diameter of the second tubular member, similar to a coarctation device, as described in Barbut, U.S. application Ser. No. 09/260,371, filed Mar. 1, 1999, incorporated herein by reference in its entirety.

In another method using the venous return cannula, the cannula is inserted through an incision on a peripheral vein, e.g., the right or left subclavian vein. The inflatable chamber is positioned at the junction of the right and left subclavian veins with the superior vena cava. The chamber is inflated so that the first and second ports on the chamber engages, respectively, the right and left subclavian veins. Venous blood flows from the right subclavian and left subclavian veins through the first and second ports and into the superior vena cava, whereas the hypothermic blood infused through the aortic shunt into the carotid arteries is passed from the jugular veins into the port(s) at the distal end of the cannula. Removed venous blood is then re-cooled and pumped back into the cerebral circulation via the aortic shunt. In this way, isolation of cerebral and systemic circulation is maintained.

It will be understood that there are many advantages in using the partial aortic occlusion devices and methods disclosed herein. For example, the devices can be used (1) to provide variable partitioning of blood flow between cerebral and systemic circulation; (2) to augment and maintain cerebral perfusion in patients suffering from global or focal ischemia; (3) to prolong the therapeutic window in global or focal ischemia; (4) to accommodate other medical devices, such as an atherectomy catheter; (5) to provide selective cooling to the cerebral vasculature; and (6) by an interventional radiologist, neuroradiologist, or cardiologist in an angiogram or fluoroscopy suite.

DETAILED DESCRIPTION

Figure 1A:
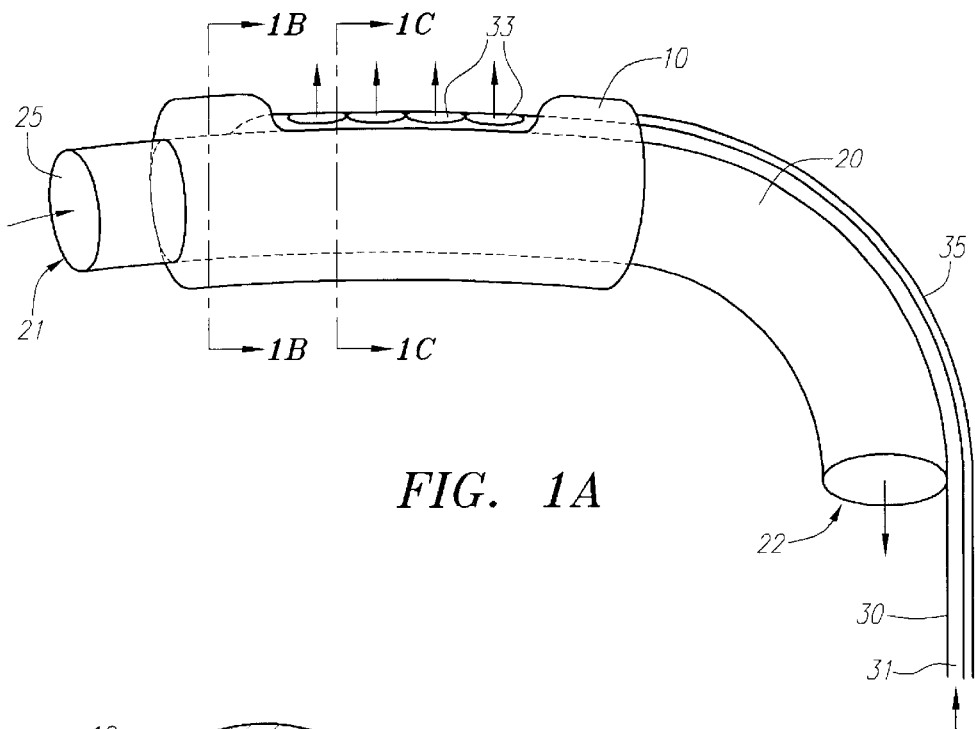
FIG. 1A depicts an embodiment of the aortic shunt according to the present invention.

An embodiment of an aortic shunt constructed according to the present invention useful for providing selective cerebral perfusion in patients suffering from stroke and cardiac arrest is depicted in FIG. 1. The shunt comprises first tubular member 20 and second tubular member 30 nested within the first member. The first member has lumen 25 that communicates with proximal opening 21 and distal opening 22 and is adapted to receive aortic blood flow. The first member also includes a side opening adapted to communicate with the carotid arteries. An expansion mechanism 10, such as an inflation seal, cylindrical balloon, or toroidal balloons, is mounted on first tubular member 20 and communicates with inflation lumen 35. The aortic shunt can be collapsed to facilitate its insertion and passage through the aorta and can be expanded to frictionally engage the lumen of the aorta by infusing air, gas, or saline through inflation lumen 35.

Second tubular member 30 has a proximal end, a distal end, and lumen 31. The distal end communicates with at least one port mounted on an intermediate portion of first tubular member 20. The port(s) are adapted to communicate with the carotid arteries. The proximal end extends outside of the patient's body and is adapted to receive oxygenated and/or hypothermic blood. FIGS. 1B and 1C provide cross-sectional views of the aortic shunt of FIG. 1A through sectional line B—B and C—C, respectively.

Figure 2A:
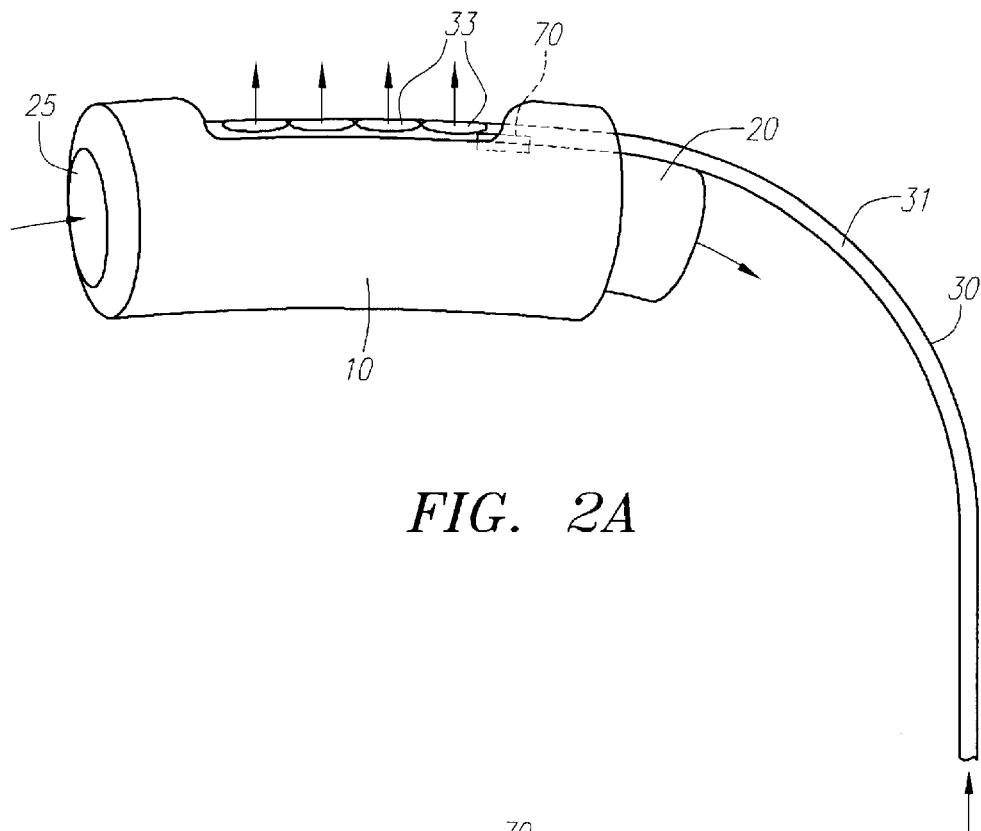
FIG. 2A depicts a lateral view of another embodiment of the aortic shunt having a shorter lumen for passage of aortic blood flow.
Figure 2B:
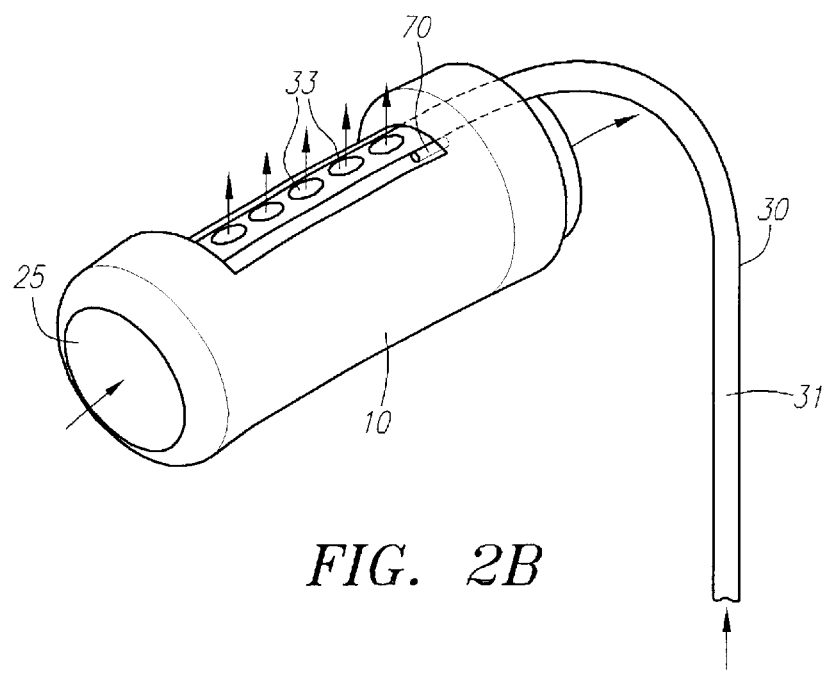
FIG. 2B depicts an oblique view of the aortic shunt of FIG. 2A.

FIGS. 2A and 2B depict a lateral and an oblique view of another embodiment of the aortic shunt. The shunt comprises second tubular member 30 nested within first tubular member 20. Lumen 25 of first tubular member 20 is adapted to receive aortic blood flow. Lumen 31 of second tubular member 30 is adapted to receive oxygenated and/or hypothermic blood which is passed through ports 33 to perfuse the carotid arteries. Manometer 70 is included in second tubular member 30 for measuring the pressure of the perfused blood. The first tubular member depicted in FIGS. 2A and 2B has a length that is shorter than that of the first tubular member in FIG. 1A. The length of the first tubular member generally spans from the ascending aorta upstream of the right brachiocephalic artery to the descending aorta downstream of the left brachiocephalic artery.

Figure 3:
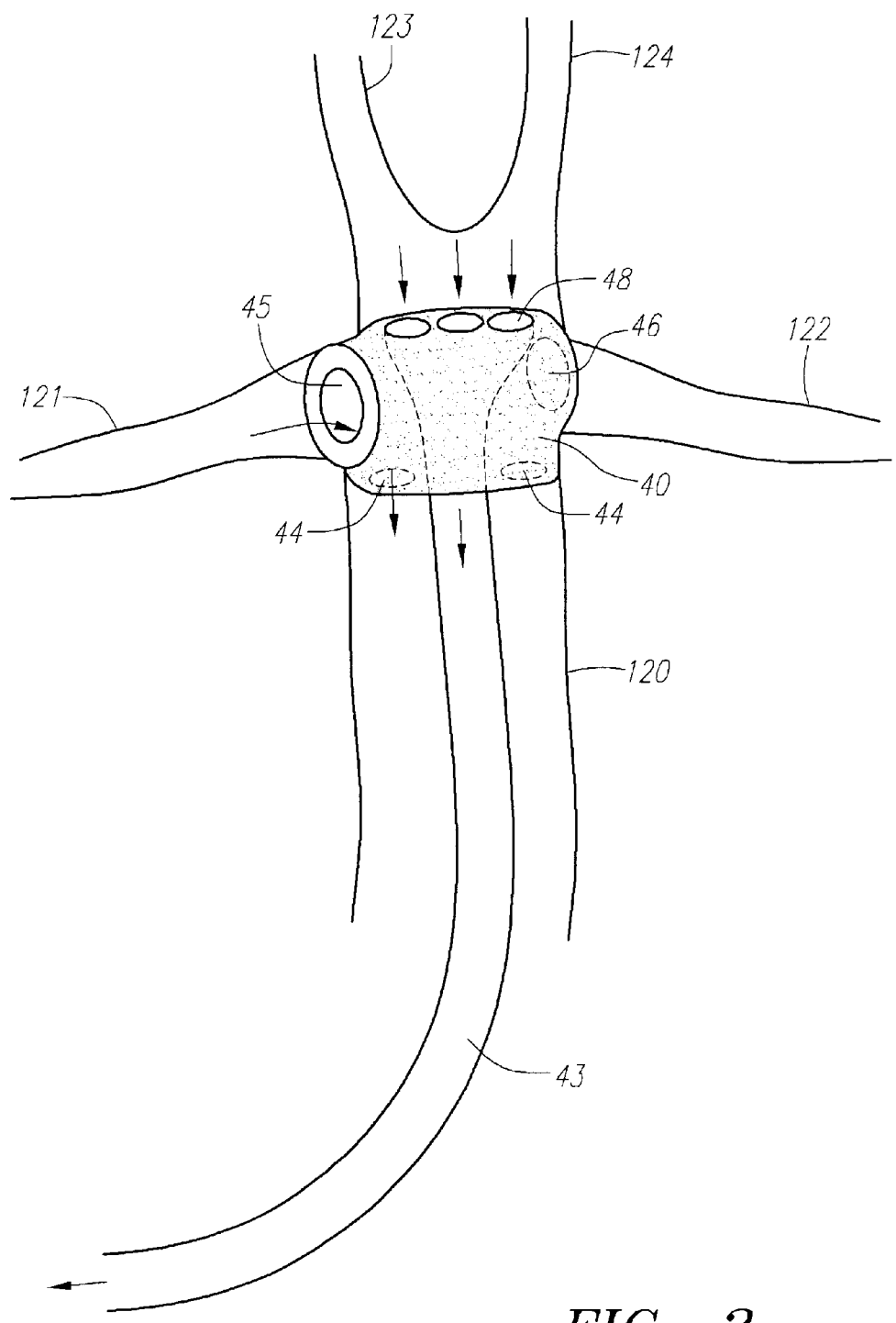
FIG. 3 depicts an embodiment of a venous return cannula inserted in the superior vena cava.

An embodiment of the venous return cannula that facilitates removal of hypothermic venous blood from the cerebral circulation is depicted in FIG. 3. The cannula comprises an elongate tubular member having a proximal end, a distal end, and lumen 43. The lumen communicates with 1, 2, 3, 4, 5, 6, 7, 8, or any other number of distal ports 48 which are adapted to receive venous blood from right jugular vein 123 and left jugular vein 124. The distal end of the cannula has inflatable chamber 40 that communicates with an inflation lumen (not shown) and upon expansion, is adapted to engage the lumen of right subclavian vein 121 and the lumen of left subclavian vein 122. Inflatable chamber 40 comprises first port 45 and second port 46, which are adapted to receive blood from right subclavian artery 121 and left subclavian artery 122, and pass the received blood into superior vena cava 120 through ports 44. In this way, the cannula maintains isolation of hypothermic jugular circulation from the subclavian circulation.

Figure 1B:
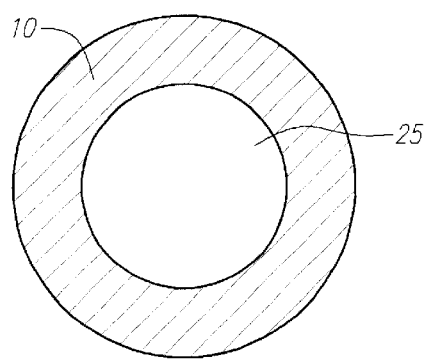
FIG. 1B depicts a cross-sectional view of the aortic shunt of FIG. 1A through line B—B.
Figure 1C:
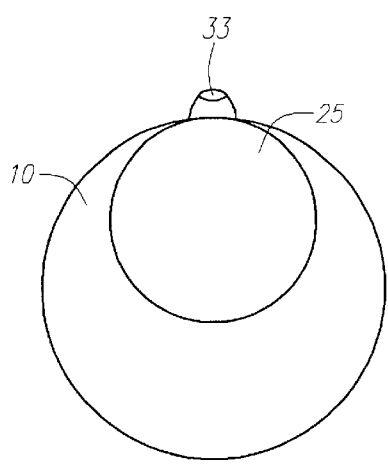
FIG. 1C depicts a cross-sectional view of the aortic shunt of FIG. 1A through line C—C.
Figure 4:
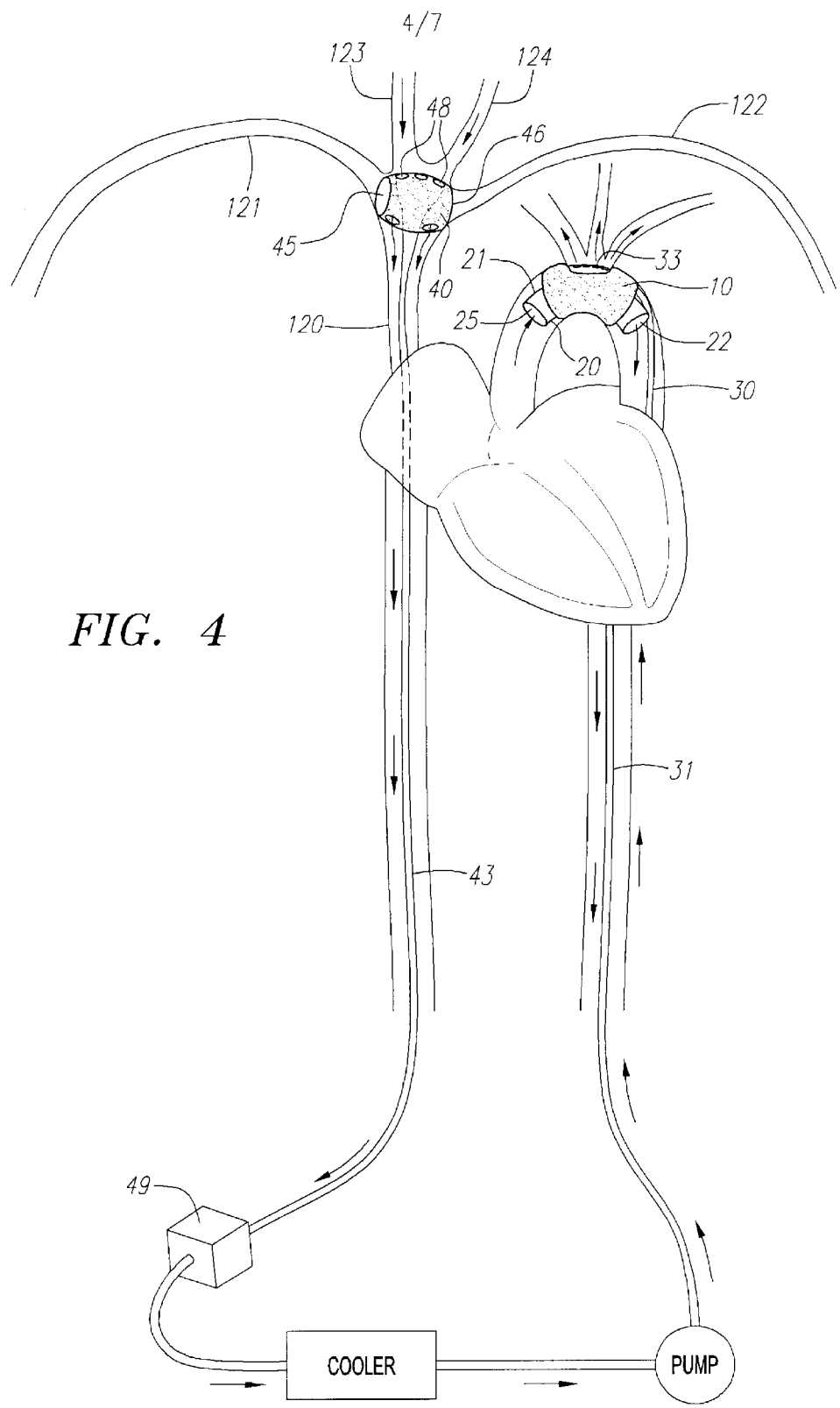
FIG. 4 depicts the aortic shunt of FIG. 1A and the venous return cannula of FIG. 3 performing selective cerebral perfusion.

FIG. 4 depicts the use of the aortic shunt of FIG. 1A and the venous return cannula of FIG. 3 in providing selective cerebral perfusion. The aortic shunt, placed in a collapsed state, is first inserted into the aorta through a peripheral artery, e.g., the femoral artery. The shunt is positioned such that proximal opening 21 of first tubular member 20 is upstream of the right brachiocephalic artery, distal opening 22 is downstream of the left brachiocephalic artery, and distal port(s) 33 of second tubular member 30 communicate with the carotid arteries. First tubular member 20 is then expanded to engage the lumen of the aorta. Oxygenated blood, optionally cooled by an external cooler, is infused through lumen 31 and ports 33 of second tubular member 30 to perfuse the cerebral vasculature, while oxygenated blood entering the ascending aorta is passed through proximal opening 21, lumen 25, and exits distal opening 22 to perfuse the peripheral organs.

In use, the venous return cannula of FIG. 3 is inserted through a peripheral vein, e.g., the femoral vein, to position inflatable chamber 40 at the junction of right subclavian vein 121 and left subclavian vein 122 within superior vena cava 120. The chamber is inflated so that first port 45 engages the lumen of right subclavian vein 121 and second port 46 engages the lumen of left subclavian vein 122. Blood flows from the right and left subclavian veins through the first and second ports into the superior vena cava. Hypothermic blood infused to the cerebral vasculature is returned to right jugular vein 123 and left jugular vein 124 and passed into ports 48 at the distal end and lumen 43 of the elongate tubular member. The removed deoxygenated blood is passed through bypass-oxygenator machine 49, a cooler, a pump, and the cooled oxygenated blood is returned to the cerebral circulation through second tubular member 30 of the aortic shunt. The circuit of blood flow provided by the aortic shunt and the venous return cannula isolates cerebral circulation from systemic circulation, thereby providing selective cerebral perfusion and avoiding complications associated with systemic cooling, e.g., disseminated intravascular coagulation.

It will be understood that the aortic shunt disclosed herein can be used independently without the use of the venous return cannula. A warming blanket is generally required to keep systemic body temperature at approximately 37° C.

Figure 5:
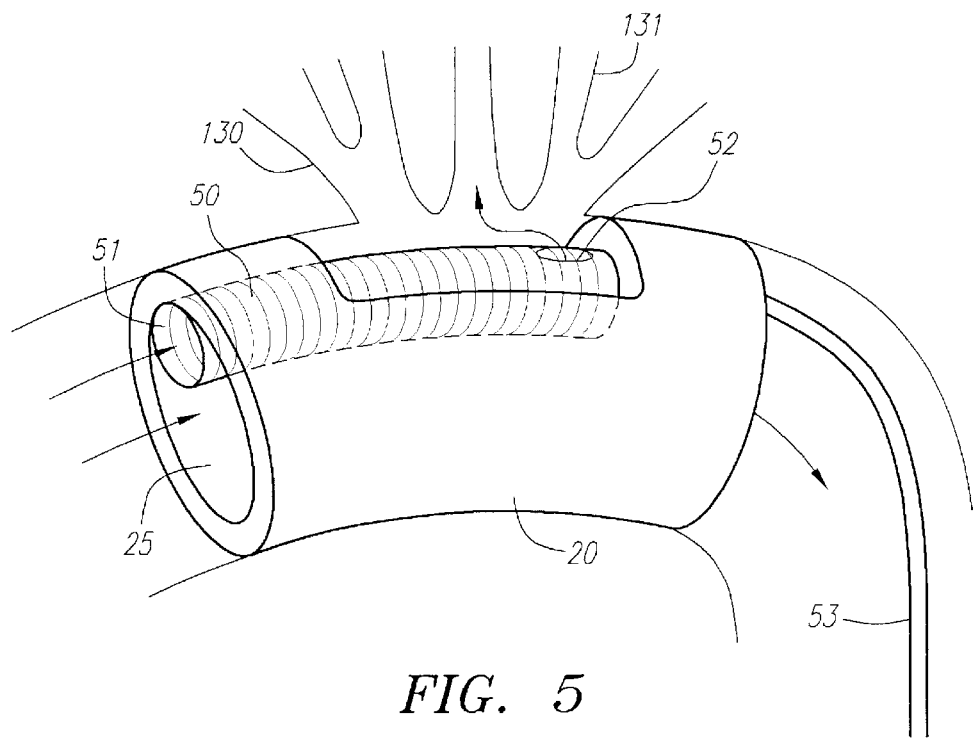
FIG. 5 depicts another embodiment of the aortic shunt including a cooling coil.

Another embodiment of the aortic shunt having a cylindrical cooling coil is depicted in FIG. 5. Cooling cylinder 50, having a proximal end, a distal end, and lumen 51, is nested within lumen 25 of expandable first tubular member 20. The distal end of the cooling coil has distal port 52 that communicates with the side opening of the first tubular member. The cooling coil is generally surrounded by an insulating sleeve. In other embodiments, the distal end has a plurality of distal ports. The distal end of first tubular member 20 communicates with inflation lumen 53. Internal cooling using a cooling coil is advantageous over external cooling using a cooler in that risk of infection introduced by external equipment and tubing is minimized.

Figure 6:
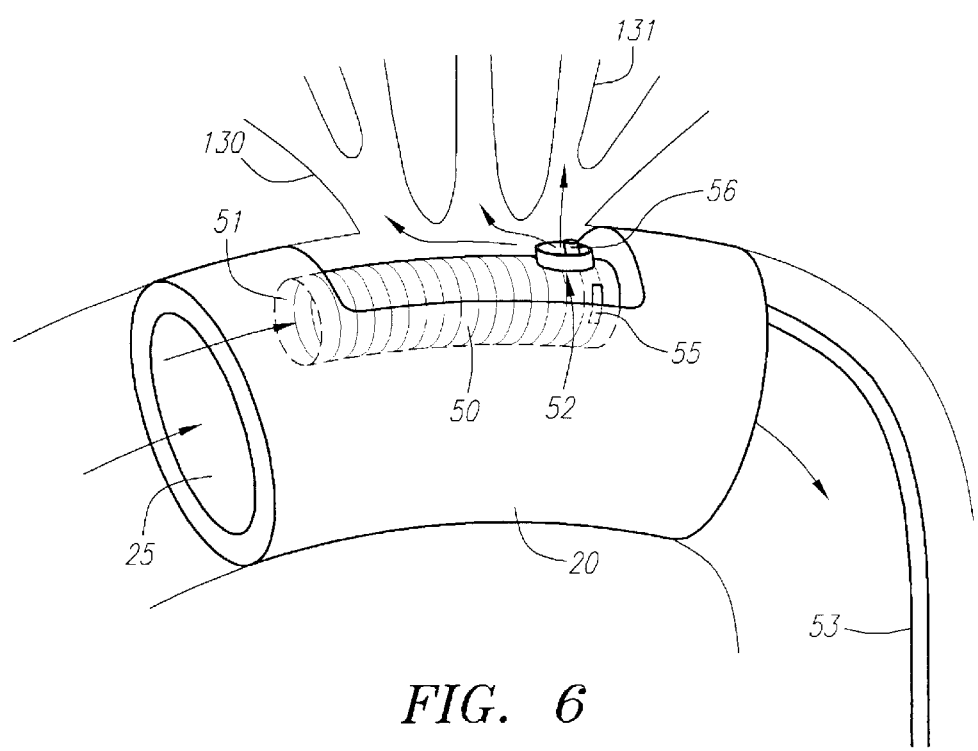
FIG. 6 depicts another embodiment of the aortic shunt having a thermostat and a thermometer mounted in its cooling coil.

In another embodiment, a thermometer and a thermostat are included in the cooling cylinder as depicted in FIG. 6. Thermometer 56, which measures the temperature of the hypothermic blood exiting cooling cylinder 50 and entering the carotid circulation, is mounted on the distal end of the cylinder. In certain embodiments, the cooling cylinder also includes a collar (not shown) capable of varying the aperture of lumen 51 of the cooling cylinder, thereby adjusting flow rates of hypothermic blood exiting distal port 52. Adjustable thermostat 55 communicates with thermometer 56 and the collar to provide variable and controlled hypothermic perfusion to the brain.

In use, first tubular member 20 is inserted and positioned in the aorta such that the proximal opening of the first tubular member is upstream of right brachiocephalic artery 130, the distal opening of the tubular member is downstream of left brachiocephalic artery 131, and distal port 52 of cooling cylinder 50 communicates with the carotid arteries. First tubular member 20 is then expanded to engage the lumen of the aorta. Oxygenated blood flows from the ascending aorta through lumen 51 of cooling cylinder 50 into the carotid arteries to perfuse the cerebral vasculature. Aortic blood entering the ascending aorta also flows through lumen 25 of first tubular member 20 into the descending aorta to perfuse the peripheral organs, protected from the effects of cerebral cooling. The cooling cylinder is capable of accommodating approximately up to 1 liter/min of the normal cerebral blood flow. As cooling proceeds, the flow rate of hypothermic blood can be reduced to a minimum of approximately 200 milliliter/min (the amount required by a cooler brain) by adjusting the collar, thereby reducing the aperture of the cooling cylinder. The smaller aperture of the cooling cylinder is generally desirable for insertion of the aortic shunt through a peripheral artery.

Figure 7:
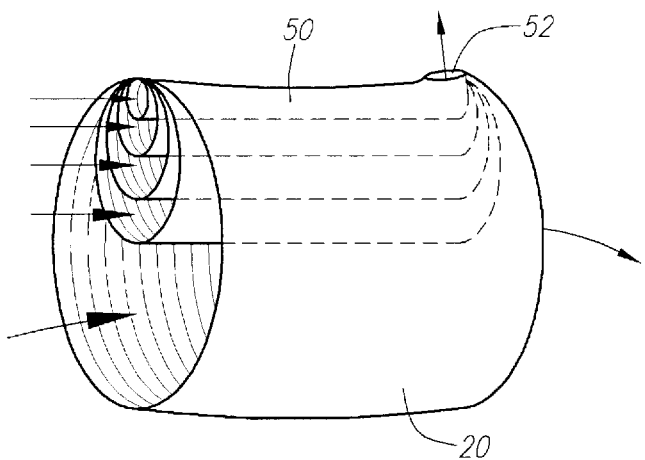
FIG. 7 depicts another embodiment of the aortic shunt capable of varying the diameter of the cooling coil.

In another embodiment, the cooling cylinder is constructed to have variable diameters to accommodate blood flow from 200 cc/min to 3 liters/min through distal port 52 as depicted in FIG. 7. As the inner diameter of the cooling cylinder increases, the proportion of aortic blood and hence cardiac output channeled into the brain increases, thereby increasing cerebral perfusion. In a dysregulated brain, this translates into increased cerebral blood flow, i.e., coarctation of the aorta. In this way, both cerebral cooling and increased cerebral perfusion can be accomplished simultaneously. In circumstances where hypothermic perfusion is not desired, the cooling system can be turned off while increased cerebral perfusion continues.

Figure 8:
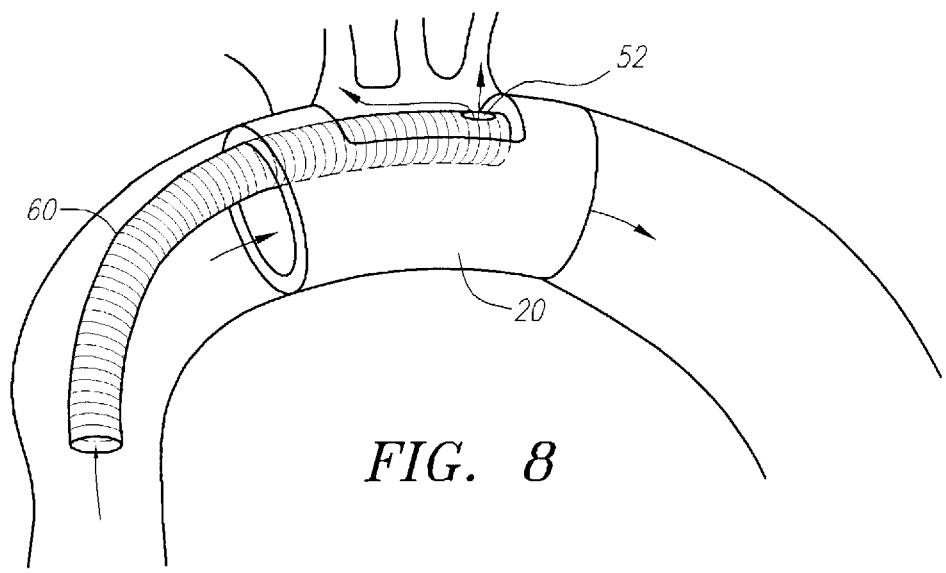
FIG. 8 depicts another embodiment of the aortic shunt having an extended cooling coil.

A cooling cylinder having the length of approximately 5 to 7 cm usually is not long enough to provide sufficient cooling at 1 Liter/min. FIG. 8 depicts another embodiment of the aortic shunt having tubular member 60 extending proximally into the ascending aorta to provide additional length for cooling. The added tubular member can have a length of up to approximately 10 cm.

Figure 9:
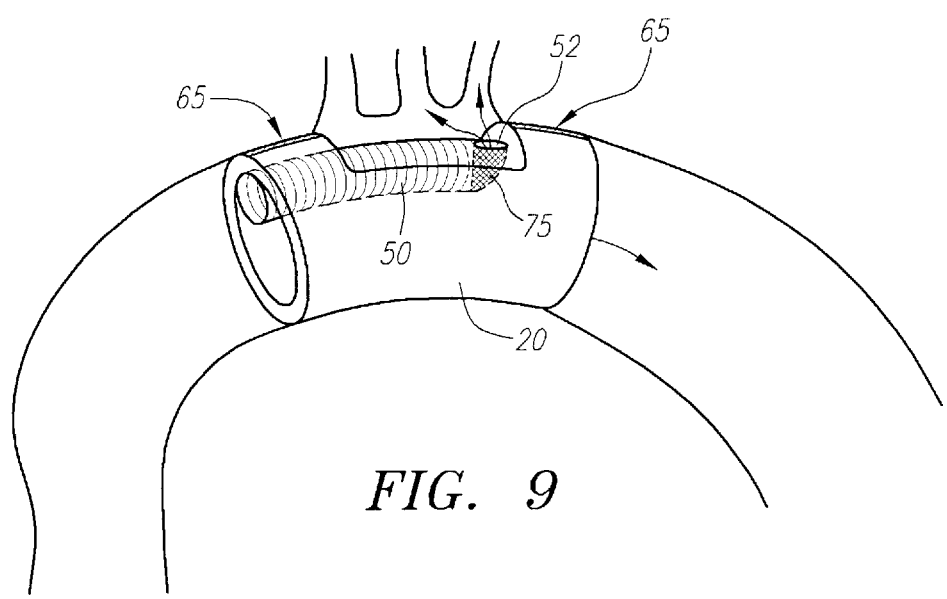
FIG. 9 depicts another embodiment of the aortic shunt having radiopaque markers mounted on its inflation seal.

In another embodiment, the aortic shunt includes radiopaque markers 65 mounted on the proximal and distal ends as depicted in FIG. 9. The markers ensure correct positioning of the shunt in the aorta, i.e., on either side of the cerebral takeoffs. Cooling cylinder 50 also includes pump 75 for enhancing blood flow through distal port 52. The pump is especially helpful in patients with low cardiac output, such as in cardiac arrest. Suitable pumps are described in Barbut, U.S. application Ser. No. 09/362,992, filed Jul. 27, 1999, incorporated herein by reference in its entirety.

Figure 10A:
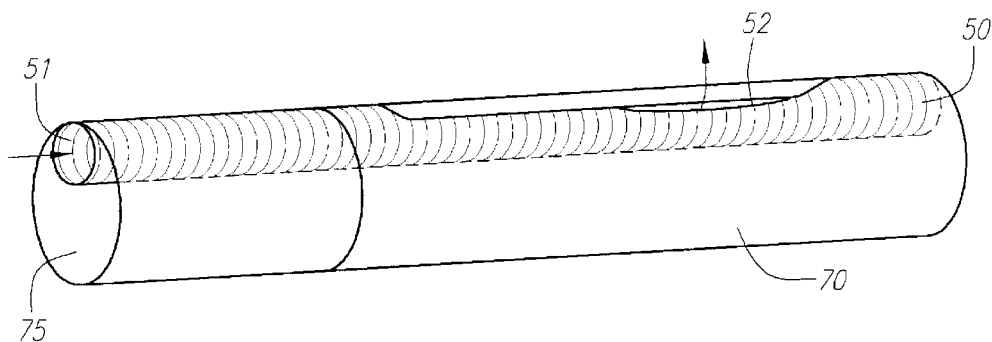
FIG. 10A depicts another embodiment of the aortic shunt integrated within an expandable stent.
Figure 10B:
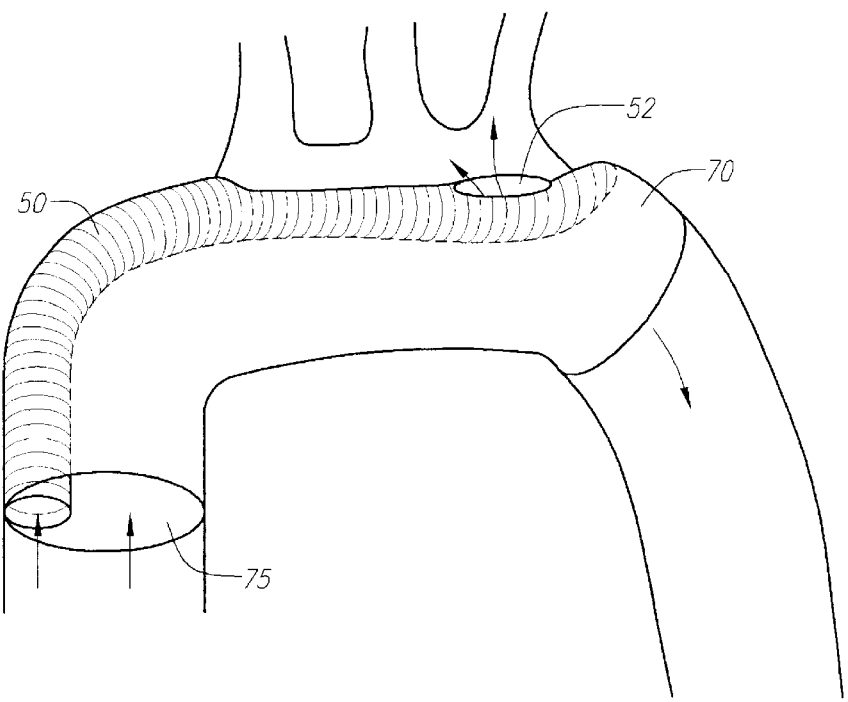
FIG. 10B depicts the aortic shunt of FIG. 10A deployed in the aorta.

In another embodiment, the cooling cylinder is mounted within a stent as depicted in FIGS. 10A and 10B. The stent is made of a self-expanding material, e.g., nitinol, or may be expanded by a stent deployment catheter. In use, the aortic shunt, having stent 70 in a collapsed state, is inserted and positioned in the aorta such that the proximal opening of the stent is upstream of the right brachiocephalic artery, the distal opening of the stent is downstream of the left brachiocephalic artery, and distal port 52 of cooling cylinder 50 communicates with the carotid arteries. Stent 70 is then expanded to engage the lumen of the aorta. Oxygenated blood flows from the ascending aorta through lumen 51 of cooling cylinder 50 into the carotid arteries (at approximately 1 Liter/min) to perfuse the cerebral vasculature. Aortic blood entering the ascending aorta also flows through lumen 75 of stent 70 (at approximately 4 Liters/min) into the descending aorta. In this manner, selective hypothermic cerebral perfusion is achieved.

The length of the aortic shunt will generally be between 3 to 20 centimeters, preferably approximately between 10 and 15 centimeters. The inner diameter of the expanded aortic shunt will generally be between 2 and 4.5 centimeters, preferably approximately between 3.0 and 3.5 centimeters. The length of the cooling cylinder will generally be between 3 to 20 centimeters, preferably approximately 10 and 15 centimeters. The inner diameter of the cooling cylinder will generally be between 0.3 and 3.0 centimeters, preferably approximately between 0.5 and 1.5 centimeters. The foregoing ranges are set forth solely for the purpose of illustrating typical device dimensions. The actual dimensions of a device constructed according to the principles of the present invention may obviously vary outside of the listed ranges without departing from those basic principles.

Although the foregoing invention has, for the purposes of clarity and understanding, been described in some detail by way of illustration and example, it will be obvious that certain changes and modifications may be practiced which will still fall within the scope of the appended claims. It will also be understood that any feature or features from any one embodiment, or any reference cited herein, may be used with any combination of features from any other embodiment.

What is claimed is:

1. An aortic shunt, comprising:
   a first tubular member expandable between a first diameter suitable for passage through the lumen of the aorta and a second diameter that frictionally engages the lumen of the aorta, the first tubular member having a length that spans from the ascending aorta upstream of the brachiocephalic trunk to the descending aorta downstream of the left subclavian artery, the first tubular member having a proximal opening, a distal opening, and a lumen therebetween, the first tubular member having a side opening adapted to communicate with the carotid arteries; and
   a second tubular member nested within the first tubular member, the second tubular member having a proximal opening, a distal opening, and a lumen therebetween, the distal opening of the second tubular member communicating with the side opening of the first tubular member, the proximal opening of the second tubular member oriented in the same direction as the proximal opening of the first tubular member,
      wherein, during use, blood flow enters the proximal opening of the first tubular member, a first portion of the blood flow enters the proximal opening of the second tubular member and flows to the carotid arteries, and a second portion of the blood flow passes through the distal opening of the first tubular member into the descending aorta.

2. The aortic shunt of claim 1, wherein the second tubular member further comprises a cooling coil, and wherein blood passing through the second tubular member is cooled before flowing into the carotid arteries.

3. The aortic shunt of claim 2, wherein the cooling coil is surrounded by an insulating sleeve.

4. The aortic shunt of claim 2, further comprising a thermometer mounted in the cooling coil.

5. The aortic shunt of claim 1, further comprising a manometer mounted in the first tubular member.

6. The aortic shunt of claim 1, further comprising a manometer mounted in the second tubular member.

7. The aortic shunt of claim 1, wherein the second tubular member further comprises a pump.

8. The aortic shunt of claim 1, wherein the second tubular member further comprises a mechanism for adjusting a diameter of the second tubular member to enable the second tubular member to regulate the amount of blood flow to the carotid arteries.

9. The aortic shunt of claim 1, wherein the first tubular member is a stent.

10. The aortic shunt of claim 1, wherein the first tubular member is a cylindrical balloon, and wherein the shunt further comprises an inflation lumen that communicates with the first tubular member.

11. The aortic shunt of claim 1, wherein the second tubular member extends proximally beyond the proximal opening of the first tubular memember.

12. The aortic shunt of claim 1, wherein the first tubular member further comprises radiopaque markers at the proximal end and the distal end.

13. The aortic shunt of claim 1, wherein the first tubular member further comprises a first toroidal balloon at a proximal end of the first tubular member and a second toroidal balloon at a distal end of the first tubular member.

14. A method for treating stroke and cardiac arrest, comprising the steps of:
   providing an aortic shunt comprising a first tubular member having a proximal opening, a distal opening, and a lumen therebetween, and having a side opening, and a second tubular member nested within the first tubular member, the second tubular member having a proximal opening, a distal opening, and a lumen therebetween, the distal opening of the second tubular member communicating with the side opening of the first tubular member, the proximal opening of the second tubular member oriented in the same direction as the proximal opening of the first tubular member;

advancing the aortic shunt into the aorta;

positioning the shunt so that the proximal opening of the first tubular member is upstream of the brachiocephalic trunk, the distal opening of the first tubular member is downstream of the left subclavian artery, and the side opening communicates with the carotid arteries; and expanding the shunt so that the first tubular member engages the lumen of the aorta,
wherein blood flow enters the proximal opening of the first tubular member, a first portion of the blood flow enters the proximal opening of the second tubular member and flows to the carotid arteries, and a second portion of the blood flow passes through the distal opening of the first tubular member.

15. The method of claim 14, wherein the second tubular member further comprises a cooling coil, and wherein blood passing through the second tubular member is cooled before flowing into the carotid arteries.

16. The method of claim 15, wherein the cooling coil is surrounded by an insulating sleeve.

17. The method of claim 15, further comprising a thermometer mounted in the cooling coil.

18. The method of claim 14, further comprising a manometer mounted in the first tubular member.

19. The method of claim 14, further comprising a manometer mounted in the second tubular member.

20. The method of claim 14, wherein the second tubular member further comprises a pump.

21. The method of claim 14, wherein the second tubular member further comprises a mechanism for adjusting a diameter of the second tubular member to enable the second tubular member to regulate the amount of blood flow to the carotid arteries.

22. The method of claim 14, wherein the first tubular member is a stent.

23. The method of claim 14, wherein the first tubular member is a cylindrical balloon, and wherein the shunt further comprises an inflation lumen that communicates with the first tubular member.

24. The method of claim 14, wherein the second tubular member extends proximally beyond the proximal opening of the first tubular member.

25. The method of claim 14, wherein the first tubular member further comprises radiopaque markers at the proximal end and the distal end.

26. The method of claim 14, further comprising the step of inserting the shunt into the femoral artery.

27. The method of claim 14, further comprising the step of inserting the shunt into the left subclavian artery.

28. The method of claim 21, further comprising the step of adjusting the diameter of the second tubular member.

29. The method of claim 28, wherein the diameter is adjusted so that 1 liter of blood flows through the second tubular member to the carotid arteries.

30. The method of claim 28, wherein the diameter is adjusted so that 200 ml of blood flows through the second tubular member to the carotid arteries.

31. The method of claim 14, further comprising the step of cooling the blood flowing through the second tubular member.

32. The method of claim 14, further comprising the step of pumping blood that flows through the second tubular member to augment blood flow to the carotid arteries.

33. The method of claim 28, wherein the diameter is adjusted to augment the flow of blood to the carotid arteries.

* * * * *